United States Patent [19]

Hopp et al.

[11] 4,110,430

[45] Aug. 29, 1978

[54] A METHOD OF DEODORIZING

[75] Inventors: Rudolf Hopp; Wolfgang Sturm, both of Holzminden; Fritz Steinfatt, Opladen, all of Germany

[73] Assignee: Haarmann & Reimer GmbH, Holzminden, Fed. Rep. of Germany

[21] Appl. No.: 543,201

[22] Filed: Jan. 22, 1975

[30] Foreign Application Priority Data

Feb. 2, 1974 [DE] Fed. Rep. of Germany ....... 2405004

[51] Int. Cl.$^2$ .............................................. A61K 7/32
[52] U.S. Cl. ..................................... 424/65; 252/106; 424/DIG. 5; 424/47; 424/59; 424/70; 424/76
[58] Field of Search ........................................... 424/65

[56] References Cited

U.S. PATENT DOCUMENTS 3,493,650  2/1970  Dunkel .................................. 424/65

OTHER PUBLICATIONS

Chem. Abs., 1960, vol. 54, pp. 2261i.
Chem. Abs., 1964, vol. 60, pp. 9187a and 13175g.

*Primary Examiner*—Dale R. Ore
*Attorney, Agent, or Firm*—Burgess, Dinklage & Sprung

[57] ABSTRACT

The invention concerns a germ-inhibiting, microbicidal or deodorizing composition comprising p-isopropyl- and/or p-tert.butyl-α-methyl hydrocinnamic alcohol, together with a carrier or diluent.

5 Claims, No Drawings

A METHOD OF DEODORIZING

This invention relates to the germ-inhibiting and microbicidal effect of p-isopropyl- and p-tert.-butyl-α-methyl hydrocinnamic alcohol, and to the use of these compounds as germ-inhibiting agents and deodorants.

It is known that body odour is due primarily to the bacterial flora of the skin and that, accordingly, deodorising measures are aimed at inhibiting the growth of these bacterial flora.

Accordingly, there is a need to find germ-inhibiting and microbicidal substances which can be effectively incorporated in body-care preparations and cosmetics and which, when applied to the skin, are at least partly absorbed onto it and remain there for a while to enable their germ-inhibiting and microbicidal and, hence, deodorising effect to be developed (cf. Fiedler, Der Schweiss, Verlag Cantor Aulendorf, 1968, page 426, Aerosol Report, Vol. 12, pp 540–553 (1973)).

It has now been found that p-isopropyl- and p-tert.-butyl-α-methyl hydrocinnamic alcohol show advantageous germ-inhibiting, microbicidal and deodorising activity, and that body-care preparations and cosmetics with a favourable germ-inhibiting, microbicidal and deodorising effect can be obtained by adding p-isopropyl- and/or p-tert.-butyl-α-methyl hydrocinnamic alcohol to them as germ-inhibiting, microbicidal and deodorising agents.

p-Isopropyl- and p-tert.-butyl-α-methyl hydrocinnamic alcohol correspond to the general formula (I):

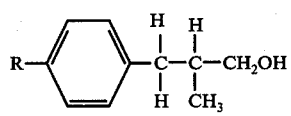

in which R represents the isopropyl or tert.-butyl radical.

These compounds have already been reported (Chem. Abstr. Vol. 54, 2261 $i$ (1960) and Vol. 60, 9187 $a$ and 13175 $g$ (1964), and are also known as 3-(4'-isopropylphenyl)- and 3-(4'-tert.-butylphenyl)-2-methyl propanol.

The germ-inhibiting and germicidal effect of the compounds of the general formula (I) according to the invention applies to bacteria, fungi and yeasts, preferably cocci and in particular staphylococci. However, their favourable deodorising effect may also be attributed to other causes.

In addition to their germ-inhibiting, microbicidal and deodorising effect, the compounds of the general formula (I) to be used according to the invention exhibit the advantage that they have fixing properties and a faint cyclamen-like odour so that they can also be used with advantage in the preparation of perfume oils. By virtue of these properties, they are also particularly suitable for use in deodorising body-care preparations and cosmetics.

The germ-inhibiting, microbicidal properties of the hydrocinnamic alcohols to be used according to the invention become apparent, when these compounds are applied in an amount of at least 0.001 mg per cm² of skin. Since the compounds are well skin-compatible the amount may be increased without difficulty to quantities of more than 0.1 mg per cm² of skin. The criterion governing the maximum quantity in which they can be applied per cm² of skin is that they should be neither uncomfortable nor uneconomic to use.

The compounds of formula (I) to be used according to the invention may be directly applied to skin for example by brushing and rubbing them on, although a solution in a skin-compatible organic solvent will generally be used. The requisite quantity may be applied in a single application or even in several succesive applications.

Because of their properties — high effectiveness, faint and pleasant odour, fixing properties, good solubility in the cosmetic bases and organic solvents normally used in body-care preparations and cosmetics, such as adipic acid diisopropyl ester, isopropyl myristate, oleic acid decyl ester, peanut oil, paraffin oil, ethanol, isopropanol, propylene glycol, methylene chloride and the like — the hydrocynnamic alcohols to be used according to the invention are especially suitable for application in body-care preparations and cosmetics. They can be incorporated without difficulties into deodorants, body-care preparations, intimate care preparations, hair-care preparations, foot-care preparations, anti-sunburn preparations, washing agents and bath additives, made up in the form of sprays, sticks, creams, Eau-de-Cologne, lotions, powders, foam baths, soaps, shampoos or the like. They can also be used in other products intended to produce a deodorising and anti-perspiration effect, such as deodorants for washing and for clothes, and room sprays.

The above stated minimum concentrations on the skin are generally achieved by incorporating the compounds of formula (I) to be used according to the invention into the above mentioned body-care preparations etc. in quantities of from 0.05 to 10% by weight, preferably of from 0.1 to 10% by weight, based on the weight of the particular preparation. The concentration of the compounds to be used according to the invention in these preparations will generally be governed by the type of preparations. The content of a foam bath concentrate which is used in a large quantity of water will be higher than the content of a preparation which is directly applied to skin for example creames, powders, lotions. The compounds of formula (I) can be incorporated by the methods normally used for producing preparations of this kind, for example by dissolution, mixing, emulsification and homogenisation.

It is primarily bacteria such as *Staphylococcus epidermis* (also known as *Staphylococcus albus*) and *Staphylococcus aureus* which are described in the literature as being germs which occur in the skin flora and which are responsible for body odour. Accordingly, any germ-inhibiting and microbicidal and, hence, deodorising agent must be effective in inhibiting the growth of the aforementioned bacteria. Table 1 below demonstrates the germ-inhibiting effect of the compounds of formula (I) according to the invention, as determined by F. Heiss's method described in SZ-PS 532,397 and Aerosol Report Vol. 12, pp 544–547 (1973).

Quantities of 0.1 ml of an alcoholic solution of the formula (I) compound identified in column 1 with the content in % by weight expressed in column 2 were applied to the contact surface of blood agar plates which had been inoculated with the germs identified in column 3. The result is expressed in column 4 as the contact growth index (CGI), 0 signifying total inhibition of germ growth over the entire contact surface.

Table I

| Column 1 Compound of general formula I: R = | Column 2 Concentration of the alcoholic solution in % by weight | Column 3 Microorganism | Column 4 CGI |
|---|---|---|---|
| $(CH_3)_2CH-$ | 1.0 | Staphylococcus epidermidis | 0 |
| $(CH_3)_2CH-$ | 1.0 | Staphylococcus aureus | 0 |
| $(CH_3)_2CH-$ | 1.0 | Candida albicans | 0 |
| $(CH_3)_3C-$ | 0.5 | Staphylococcus epidermidis | 0 |
| $(CH_3)_3C-$ | 0.5 | Staphylococcus aureus | 0 |
| $(CH_3)_3C-$ | 0.5 | Candida albicans | 0 |

Examples of the production of various body-care preparations and cosmetics are given in the following. In each Example, the preparation produced in this way was extremely effective as a deodorant when properly used.

EXAMPLE 1

A deodorant spray was prepared as follows:

An aerosol can was filled with a mixture of 38.0 g of ethanol, 1.0 g of perfume oil, 0.5 of isopropyl myristate and 0.5 g of 3-(4'-isopropylphenyl)-2-methyl propanol. After the aerosol can had been closed, 60 g of difluorodichloromethane were introduced through the valve.

EXAMPLE 2

A deodorant spray was prepared in the same way as described in Example 1, except that the 0.5 g of 3-(4'-isopropylphenyl)-2-methyl propanol was replaced by 0.5 g of 3-(4'-tert.-butyl-phenyl)-2-methyl propanol.

EXAMPLE 3

100 g of soap chips were mixed with 1 g of perfume oil and 0.5 g of 3-(4'-isopropylphenyl)-2-methyl propanol until a soap mass of substantially homogeneous composition was obtained. After homogenisation, the soap mass was moulded to form a cake of soap.

EXAMPLE 4

100 g of soap chips were mixed with 1 g of perfume oil and 0.5 g of 3-(4'-tert.-butylphenyl)-2-methyl propanol until a soap mass of substantially homogeneous composition was obtained. After homogenisation, the soap mass was moulded to form a cake of soap.

EXAMPLE 5

An intimate washing concentrate was prepared in accordance with the following recipe:

A mixture was initially prepared from (quantities in parts by weight):

2.0 of a water-soluble partial glyceride mixture of natural saturated even-numbered vegetable fatty acids with a chain length of $C_8$ to $C_{12}$, obtained by the addition of ethylene oxide (characteristics: hydrolysis No. 90-100, density at 25° C approximately 1.068, viscosity at 25° C 110-130cP), for example Softigen ©767, a product of Chemische Werke Witten; and 0.5 of 3-(4'-isopropylphenyl)-2-methyl propanol.

The mixture was heated to 60° C. The substances mentioned in the following were then added with thorough stirring in the order indicated:

60.0 of fatty acid amidomethyl betaine $C_{10} - C_{18}$ 30% aqueous solution;

0.3 of perfume oil;

28.6 of distilled water;

7.2 of sodium lauryl ether sulphate containing 2 mols of ethylene oxide; and 7.4 of sodium bicarbonate solution (10% in water).

EXAMPLE 6

An intimate washing concentrate was prepared in accordance with the following recipe:

A mixture was initially prepared from (quantities in parts by weight):

2.0 of a water-soluble partial glyceride mixture of natural saturated even-numbered vegetable fatty acids with a chain length of $C_8$ to $C_{12}$, obtained by the addition of ethylene oxide (characteristics: hydrolysis No. 90-100, density at 25° C approximately 1.068, viscosity at 25° C 100-130cP), for example Softigen ©767, a product of Chemische Werke Witten; and 0.5 of 3-(4'-tert.-butylphenyl)-2-methyl propanol.

The mixture was heated to 60° C. The substances mentioned in the following were added with thorough stirring in the order indicated:

60.0 of fatty acid amidomethyl betaine $C_{10} - C_{18}$ 30% aqueous solution;

0.3 of perfume oil;

28.6 of distilled water;

7.2 of sodium lauryl ether sulphate containing 2 mols of ethylene oxide; and 7.4 of sodium bicarbonate solution (10% in water).

We claim:

1. Method of deodorizing which comprises applying to the place to be deodorized an effective deodorising amount of a deodorising ingredient selected from the group consisting of p-isopropyl-α-methyl hydrocinnamic alcohol, p-tert. butyl-α-methyl hydrocinnamic alcohol and mixtures thereof.

2. Method for deodorising human skin comprising contacting the skin with an effective deodorising amount of a deodorising ingredient selected from the group consisting of p-isopropyl-α-methyl hydrocinnamic alcohol, p-tert. butyl-α-methyl hydrocinnamic alcohol and mixtures thereof.

3. Method according to claim 2 wherein the effective deodorising amount is at least 0.001 mg a deodorising ingredient selected from the group consisting of p-isopropyl-α-methyl hydrocinnamic alcohol, p-tert. butyl- α-methyl hydrocinnamic alcohol and mixtures thereof per cm² skin.

4. Method according to claim 2, wherein the effective deodorising amount is from 0.001 to 0.1 mg a deodorising ingredient selected from the group consisting of p-isopropyl-α-methyl hydrocinnamic alcohol, p-tert, butyl-α-methyl hydrocinnamic alcohol and mixtures thereof per cm² of skin.

5. Method according to claim 2, wherein the deodorising ingredient selected from the group consisting of p-isopropyl-α-methyl hydrocinnamic alcohol, p-tert. butyl-α-methyl hydrocinnamic alcohol and mixtures thereof is applied in the form of a solution in a skin-compatible organic solvent or in form of a body-care preparation or in the form of a cosmetic.

* * * * *